(12) United States Patent
Remondini

(10) Patent No.: US 11,307,120 B2
(45) Date of Patent: Apr. 19, 2022

(54) APPARATUS AND METHOD FOR MEASURING ODOURS

(71) Applicant: SACMI COOPERATIVA MECCANICI IMOLA SOCIETA' COOPERATIVA, Imola (IT)

(72) Inventor: Marco Remondini, Imola (IT)

(73) Assignee: SACMI COOPERATIVA MECCANICI IMOLA SOCIETA' COOPERATIVA, Imola (IT)

(*) Notice: Subject to any disclaimer, the term of this patent is extended or adjusted under 35 U.S.C. 154(b) by 0 days.

(21) Appl. No.: 15/522,651

(22) PCT Filed: Nov. 3, 2015

(86) PCT No.: PCT/IB2015/058489
§ 371 (c)(1),
(2) Date: Apr. 27, 2017

(87) PCT Pub. No.: WO2016/071834
PCT Pub. Date: May 12, 2016

(65) Prior Publication Data
US 2017/0328816 A1    Nov. 16, 2017

(30) Foreign Application Priority Data

Nov. 5, 2014 (IT) .......................... BO2014A000614

(51) Int. Cl.
*G01N 1/22* (2006.01)
*G01N 33/00* (2006.01)
(Continued)

(52) U.S. Cl.
CPC ............. *G01N 1/2273* (2013.01); *G01N 1/26* (2013.01); *G01N 27/00* (2013.01);
(Continued)

(58) Field of Classification Search
CPC ............. G01N 1/2273; G01N 33/0029; G01N 33/0001; G01N 27/00; G01N 1/00; G01N 1/26; G01N 33/0031; A61B 5/00
See application file for complete search history.

(56) References Cited

U.S. PATENT DOCUMENTS 4,884,435 A    12/1989  Ehara et al.
5,134,080 A     7/1992  Bell et al.
(Continued)

FOREIGN PATENT DOCUMENTS

EP    0317299 A2      5/1989
GB    2014411 A  *   8/1979  ............. C01B 13/11
(Continued)

OTHER PUBLICATIONS

Aguilera, T., et al., "Electronic Nose Based on Independent Component Analysis Combined with Partial Least Squares and Artificial Neural Networks for Wine Prediction", Sensors, 2012, vol. 12, pp. 8055-8072.

(Continued)

*Primary Examiner* — Ryan A Reis
(74) *Attorney, Agent, or Firm* — Pearne & Gordon LLP

(57) ABSTRACT

Described is an apparatus (1) for measuring odours comprising: a measuring chamber (2); an intake duct (4) having two ends, an inlet end (4a) in communication with the outside environment and an outlet end (4b) in connection with the measuring chamber; at least one sensor (3), positioned inside the measuring chamber (2) and designed for measuring the olfactory properties of a gas; a control unit (6) designed for processing signals coming from the at least one sensor (3) and providing a parameter representing the odours measured in the gas to be analysed; a suction device (5), positioned inside the intake duct (4) and designed to circulate the gas inside the apparatus (1); a cleaning device designed for restoring the characteristics of the at least one (Continued)

sensor (3) following a measurement, wherein the cleaning device is designed for generating ozone inside the apparatus (1).

20 Claims, 2 Drawing Sheets

(51) Int. Cl.
    *G01N 1/26* (2006.01)
    *G01N 27/00* (2006.01)
    *A61B 5/00* (2006.01)
    *G01N 1/00* (2006.01)

(52) U.S. Cl.
    CPC ..... *G01N 33/0001* (2013.01); *G01N 33/0029* (2013.01); *G01N 33/0031* (2013.01); *A61B 5/00* (2013.01); *G01N 1/00* (2013.01)

(56) References Cited

U.S. PATENT DOCUMENTS

| | | | | |
|---|---|---|---|---|
| 5,540,898 | A | * | 7/1996 | Davidson ............ C01B 13/115 422/186.15 |
| 5,801,297 | A | | 9/1998 | Mifsud et al. |
| 5,918,257 | A | | 6/1999 | Mifsud et al. |
| 8,256,264 | B2 | | 9/2012 | Bosi et al. |
| 2004/0244465 | A1 | | 12/2004 | Bresciani et al. |
| 2005/0156118 | A1 | * | 7/2005 | Chua ................... B01D 46/442 250/426 |
| 2010/0300180 | A1 | | 12/2010 | Bosi et al. |
| 2012/0070334 | A1 | * | 3/2012 | Ehrhorn ................ A23B 7/152 422/3 |
| 2013/0061692 | A1 | * | 3/2013 | Muresan ............ G01N 33/0031 73/863 |

FOREIGN PATENT DOCUMENTS

| | | | | |
|---|---|---|---|---|
| JP | | 63291805 A | * 11/1988 | ............. C01B 13/11 |
| WO | | 2009068965 A1 | 6/2009 | |

OTHER PUBLICATIONS

El Barbri, N., et al., "Electronic Nose Based on Metal Oxide Semiconductor Sensors as an Alternative Technique for the Spoilage Classification of Red Meat", Sensors, 2008, vol. 8, pp. 142-156.

Capelli, L., et al., "Electronic Noses for the Continuous Monitoring of Odours From a Wastewater Treatment Plant at Specific Receptors: Focus on Training Methods", Sensors and Actuators B: Chemical: International Journal Devoted to Research and Development of Physical and Chemical Transducers, Elsevier S.A., CH, vol. 131, No. 1, Apr. 14, 2008, XP022602864, pp. 53-62.

Licinia Dentoni, et al., "Development of an Electronic Nose for Environmental Odour Monitoring", Sensors, vol. 12, No. 12, Oct. 25, 2012, XP055240132, pp. 14363-14381.

* cited by examiner

APPARATUS AND METHOD FOR MEASURING ODOURS

TECHNICAL FIELD

This invention relates to an apparatus and a method for measuring odours.

BACKGROUND ART

This invention applies to the field of olfactory systems, also known as "electronic noses", which allow a gas coming from a particular environment to be analysed to assign a specific olfactory class or olfactarily quantify the gas analysed, estimating an odour concentration.

The odours comprise molecules, of various types, which are able to move freely inside a gas and reach the human olfactory receptors for being captured. Similarly, a gas containing these molecules may be sucked in by artificial olfactory systems, for capturing the molecules, quantifying them and classifying them.

The operation of the electronic nose follows that of the human olfactory system and is generally divided into the following steps:
measuring the gas using suitable sensors;
processing the signals coming from the sensors;
recognising the odours;
cleaning the instrument and resetting the sensors by means of a cleaning gas, with a very low (theoretically zero) concentration of odour.

The prior art electronic noses comprise an intake duct, which connects the outside environment or a sample holder (containing a predetermined volume of a gas) with a measuring chamber. The circulation of the gas through the electronic nose is usually guaranteed by a suction device. The suction device may be, for example, a pump or a fan.

The measuring chamber, usually made of a chemically inert material, houses a matrix of sensors. The calibration of the sensors of the electronic nose is performed using the passage of a reference gas (usually air) inside the measuring chamber, in such a way as to establish a baseline for the response of the sensors.

To perform a measurement, the electronic nose is fed with the gas to be analysed in the measuring chamber. That produces a variation of the chemical atmosphere in the measuring chamber and, consequently, a response of the sensors. A control unit is designed to process the signals coming from the sensors and to provide a parameter representing the odours measured in the gas to be analysed.

The measurement concludes with a step of cleaning the sensors, which comprises the introduction into the measurement chamber of a cleaning gas (of the same type as the reference gas), for resetting the sensors to the initial condition and returning the response to the baseline. The cleaning gas used is usually one or other of air, argon or nitrogen, filtered beforehand by a carbon filter for reducing the concentration of odour. Some examples of electronic noses are contained in patent document WO2009068965A1 (of the same Applicant as this invention) and in the following scientific articles:

N. El Barbri, E. Llobet, N. El Bari, X. Correig, and B. Bouchikhi, *Electronic Nose Based on Metal Oxide Semiconductor Sensors as an Alternative Technique for the Spoilage Classification of Red Meat*, Sensors 2008, 8, 142-156;

T. Aguilera, J. Lozano, J. A. Paredes, F. J. Alvarez, and J. I. Suarez, *Electronic Nose Based on Independent Component Analysis Combined with Partial Least Squares and Artificial Neural Networks for Wine Prediction*, Sensors 2012, 12, 8055-8072.

Other examples of apparatus for measuring odours are known form patent documents U.S. Pat. Nos. 5,134,080, 5,801,297, US2004/244465 and EP0317299.

However, the prior art electronic noses have significant drawbacks.

The odour molecules, being free in the air, can bond with solid receptor bodies, for example, the sensors of the measuring chamber, with more or less strong electromagnetic bonds. The energy associated with the bond depends both on the nature of the free molecules and on the nature of the solid bodies. This bond is known with the term "molecular retention".

One of the main drawbacks linked with the molecular retention consists in a slowing down of resetting the system during the step for cleaning the sensors, for preparing the instrument for a subsequent measurement. If the gas to be analysed is characterised by a high concentration of very persistent odours, due to the molecular retention it is necessary to flush the ducts and the measuring chamber of the device used for several hours with the cleaning gas.

The impact of this drawback becomes particularly critical during training of the electronic nose. During the training step, a sample of gas to be analysed, having an unknown concentration, is inserted in the measuring chamber to check the suitability for use in the training. It can occur that the sample of gas to be analysed, sampled using a bag (usually made of nalophan) from, for example, waste or a composting system, is characterised by an extremely intense odour, even two orders of magnitude greater than the purpose.

After the preliminary analysis of the sample of gas using the electronic nose, it is necessary to assess whether/how much to dilute the sample in order to make it suitable for training the nose. To perform this step correctly, the sensors of the electronic nose must be perfectly reset, and able to correctly perform the measurements. In this case, the resetting of the electronic nose requires the flushing of the ducts and the measuring chamber with cleaning gas for several hours.

With the prior art electronic noses it is difficult to perform two trainings in a single working day. This is often considered unacceptable by the operators in charge of training the electronic nose, who are often forced to carry out imprecise training with consequently poor results in the operation of the electronic nose.

DISCLOSURE OF THE INVENTION

The aim of this invention is to provide an apparatus and a method for measuring odours which overcome the above-mentioned drawbacks of the prior art.

More specifically, the aim of this disclosure is to provide an apparatus and a method for measuring odours in a particularly fast and effective manner.

A further aim of this disclosure is to provide an apparatus and a method for measuring odours which is particularly efficient and reliable.

These aims are fully achieved by the apparatus and by the method for measuring odours according to this disclosure, as characterised in the appended claims. More specifically, the apparatus for measuring odours according to the disclosure comprises a measuring chamber. The apparatus also comprises at least one sensor positioned inside the measuring chamber. The sensor is designed to measure the odours and the olfactory properties of a gas.

The gas is introduced in the measuring chamber through an intake duct having two ends. A first end (that is, the inlet end) is in communication with the outside environment. Alternatively, the first end is connected to a sample holder. A second end (that is, the outlet end) is in connection with the measuring chamber.

The apparatus also comprises a suction device (for example a pump or a fan), designed to circulate the gas inside the apparatus. Preferably, the suction device is located inside the intake duct.

The apparatus for measuring odours comprises a control unit designed for processing the signals coming from the at least one sensor and providing a parameter representing the odours measured in the gas.

The apparatus also comprises a cleaning device, designed for restoring the characteristics of the at least one sensor following a measurement. The cleaning device is designed to supply a controlled flow of ozone inside the apparatus.

It should be noted that the use of ozone for the cleaning process avoids the presence of cylinders, which are necessary for storing other industrial gases. The ozone is in effect an unstable gas and must be produced on site.

It should also be noted that the use of ozone avoids the process for filtering the cleaning gas, and, therefore, the presence of carbon filters.

Furthermore, thanks to the device, the time needed to reset the system is reduced to a few dozen minutes, thereby allowing the times for training the electronic nose to be reduced significantly. The cleaning of the sensors by means of ozone is in effect much more effective.

Preferably, the cleaning device is designed to supply a controlled flow of ozone. Even more preferably, the cleaning device comprises an ozone generator.

The use of an ozone generator of a commercial type may prove harmful for the at least one sensor. The high concentration of ozone produced could lead to accelerated ageing of the at least one sensor and could result in damage to the seals of the suction device. The ozone generator produces the ozone at a predetermined point of the apparatus. The suction device circulates the ozone produced by the ozone generator generating a flow of ozone inside the apparatus.

Preferably, the ozone generator comprises an anode and a cathode located at a predetermined distance and connected to a high voltage generator, in order to ionize the gas and produce the ozone.

The high voltage generator is preferably limited in terms of current.

Preferably, the cathode and the anode are in a point-to-plane configuration and are facing each other inside the intake duct. The production of the ozone is thus the result of the triggering of corona effect discharges.

Preferably, the control unit is connected to the ozone generator to vary the rate of the production of ozone and check that its production does not exceed a predetermined limit, beyond which there might be accelerated ageing phenomena of the at least one sensor or damage to the seals of the suction device.

Even more preferably, the control unit is connected to a current measuring device. The current measuring device measures the value of current delivered by the high voltage generator. The control unit, connected to the voltage generator, varies the voltage between the electrodes and consequently the current delivered by the generator, for controlling the rate of the production of ozone.

It should be noted that the control of the ozone concentration according to this disclosure is more rapid, precise and effective compared to a controlled mixing with a suitably filtered cleaning gas.

It should also be noted that a live control of the high voltage generator would be less efficient. The voltage should first exceed that of triggering and then be lowered, with the risk of interrupting the phenomenon.

Preferably, the cleaning device is located close to the inlet end of the intake duct. It should be noted that by positioning conveniently the ozone generator inside the apparatus it is possible to clean the measuring chamber in an effective fashion and remove from the intake duct any residual odour.

Preferably, the apparatus according to the disclosure comprises a plurality of measuring chambers, connected in parallel to the intake duct, to perform differential measurements.

This disclosure also relates to a method for measuring odours comprising the steps of:
  introducing a gas inside a measuring chamber, by means of an intake duct connected to a suction device;
  measuring any odours in the gas using at least one sensor located inside the measuring chamber;
  flushing ozone inside the apparatus, to reset the at least one sensor.

It should be noted that the disclosure, thanks to the use of ozone, allows the user to restore the at least one sensor after a measurement in a particularly fast and effective fashion.

The presence in the apparatus of a control unit, designed to control the quantity of ozone generated, makes the solution even more reliable, preventing the excessive wear of the sensors.

The presence of an ozone generator located on board the machine (i.e. the ozone generator is part of the machine, that is, it is positioned within the machine and is not a separate external entity) makes the solution particularly efficient, avoiding an otherwise necessary controlled mixing with a suitably filtered cleaning gas.

More specifically, if the ozone generator comprises two electrodes facing each other inside the intake duct and connected to a high voltage generator to define an anode and a cathode, in a point-to-plane configuration, the generation of an electric field inside the intake duct makes the generation of ozone particularly simple and inexpensive. More specifically, the point-to-plane configuration of the electrodes allows ozone to be generated at a voltage less than that of other electrode configurations.

Preferably, the control of the rate of generation of ozone comprises the measurement of a current delivered by the generator and the variation of the voltage between anode and cathode. In this way, the control unit (or the user) can adjust the production of ozone quickly and easily, by varying the voltage between the electrodes, as a function of the current delivered by the generator.

During training of the electronic nose, the use of ozone is particularly advantageous for the user, who can rapidly restore the at least one sensor and carry out several trainings in a working day. In this case, the method for measuring odours comprises the steps of:
  picking a sample of gas characterised by a high concentration of odour;
  estimating the concentration of odour using at least one sensor located inside a measuring chamber;
  diluting the gas sample to reduce the concentration of odour;
  flushing ozone inside the apparatus, to reset the at least one sensor;

introducing diluted gas inside the measuring chamber for training the control unit of the apparatus to recognise the characteristic odour of the gas sample.

BRIEF DESCRIPTION OF DRAWINGS

This and other features of the disclosure will become more apparent from the following detailed description of a preferred, non-limiting example embodiment of it, with reference to the accompanying drawings, in which.

DETAILED DESCRIPTION OF PREFERRED EMBODIMENTS OF THE INVENTION

Figure 1:
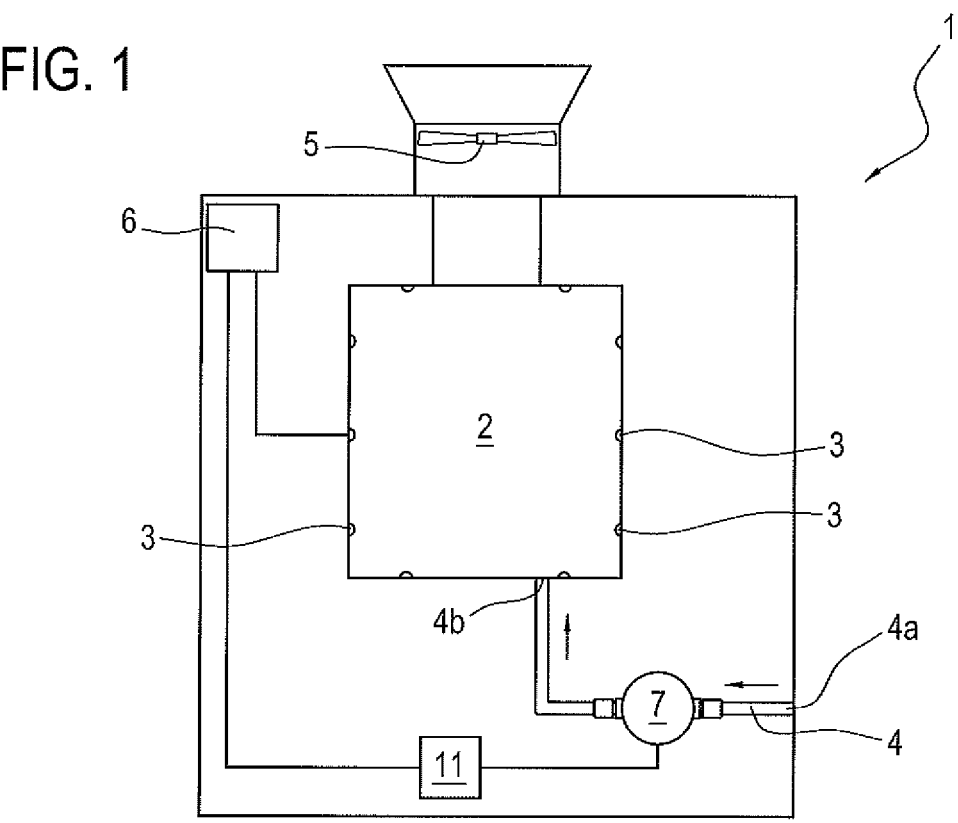
FIG. 1 is a schematic representation of an apparatus according to this disclosure.
Figure 2:
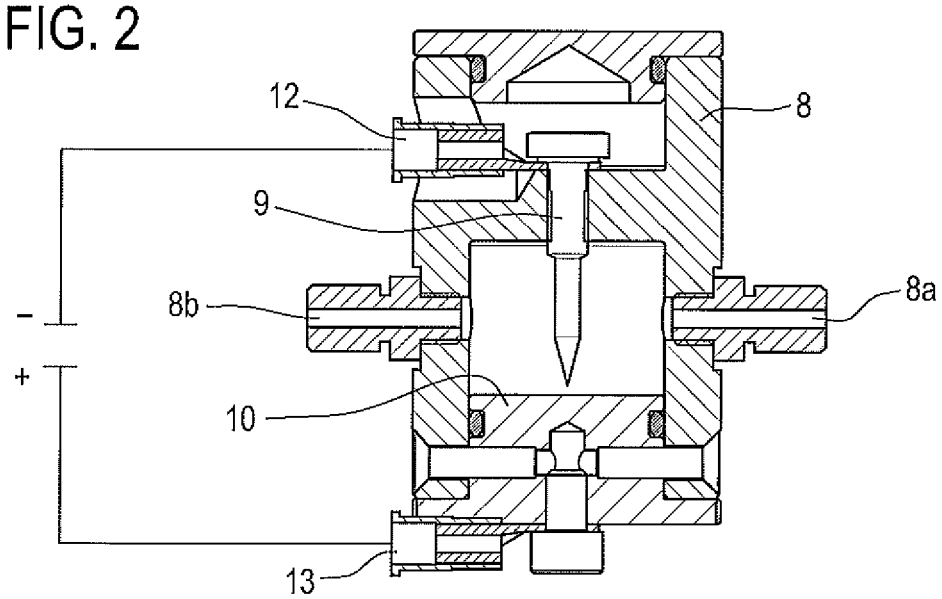
FIG. 2 is a side view in cross section of a detail of the apparatus of FIG. 1.

With reference to the drawings, the numeral 1 denotes an apparatus for measuring odours.

The apparatus 1 comprises a measuring chamber 2. At least one sensor 3, positioned inside the measuring chamber 2, is designed for measuring the odours and the olfactory properties of a gas. In the embodiment illustrated, the measuring chamber 2 comprises a plurality of sensors 3, positioned in proximity to the walls of the measuring chamber 2. The apparatus 1 also comprises an intake duct 4 having two ends. A first end 4a (that is, the inlet end) is in communication with the outside environment. In one particular embodiment, the first end 4a is connected to a sample holder. A second end 4b (that is, the outlet end) is in connection with the measuring chamber 2.

The apparatus 1 also comprises a suction device, designed to circulate the gas inside the apparatus. Preferably, the suction device is located inside the intake duct. In the embodiment illustrated, the apparatus 1 comprises a suction device 5 (for example a pump or a fan) located downstream of the measuring chamber 2 for drawing gas to be analysed through the intake duct 4 inside the measuring chamber 2.

The apparatus 1 for measuring odours comprises a control unit 6 designed for processing the signals coming from the at least one sensor 3 and providing a parameter representing the odours measured in the gas.

In the embodiment illustrated, the apparatus 1 comprises an ozone generator 7. The ozone generator is designed for producing the ozone at a predetermined point of the apparatus 1. The suction device 5 circulates the ozone produced by the ozone generator 7 generating a flow of ozone inside the apparatus 1.

In the embodiment illustrated, the ozone generator 7 is positioned in the intake duct 4, in the proximity of the inlet end 4a. The ozone generator 7 comprises a body 8, having an inlet hole 8a and an outlet hole 8b, which houses a cathode 9 and an anode 10 located at a predetermined distance, in a point-to-plane configuration. Cathode 9 and anode 10 are connected to a high-voltage generator 11. More specifically, the electrodes 9, 10 are connected to the high voltage generator 11 by a first connector 12 and a second connector 13.

In the embodiment illustrated, the control unit 6 is connected to the high voltage generator 11. More specifically, the control unit 6 varies the voltage between the electrodes 9, 10 on the basis of the value of the current delivered by the high voltage generator 11 and consequently adjusts the rate of production of ozone.

This disclosure also relates to a method for measuring odours comprising the steps of:

introducing gas inside the measuring chamber 2, by means of an intake duct 4 connected to the suction device 5;

measuring any odours in the gas using the at least one sensor 3 located inside the measuring chamber 2;

flushing ozone inside the apparatus 1, to reset the at least one sensor 3.

Preferably, the control unit 6 is designed to control the rate of production of ozone. Even more preferably, in the embodiment wherein the apparatus comprises the ozone generator 7, the control unit 6 controls the step of activating the ozone generator 7, for generating ozone inside the apparatus 1.

More specifically, in the embodiment wherein the ozone generator 7 comprises two electrodes 9, 10 connected to a high voltage generator 11 to define a cathode 9 and an anode 10 in a point-to-plane configuration, the control unit controls the high voltage generator and therefore the generation of an electric field between cathode 9 and anode 10.

Preferably, the control of the rate of generation of ozone comprises the measurement of a current delivered by the high voltage generator 11 and the variation of the voltage between cathode 9 and anode 10.

Figure 3:
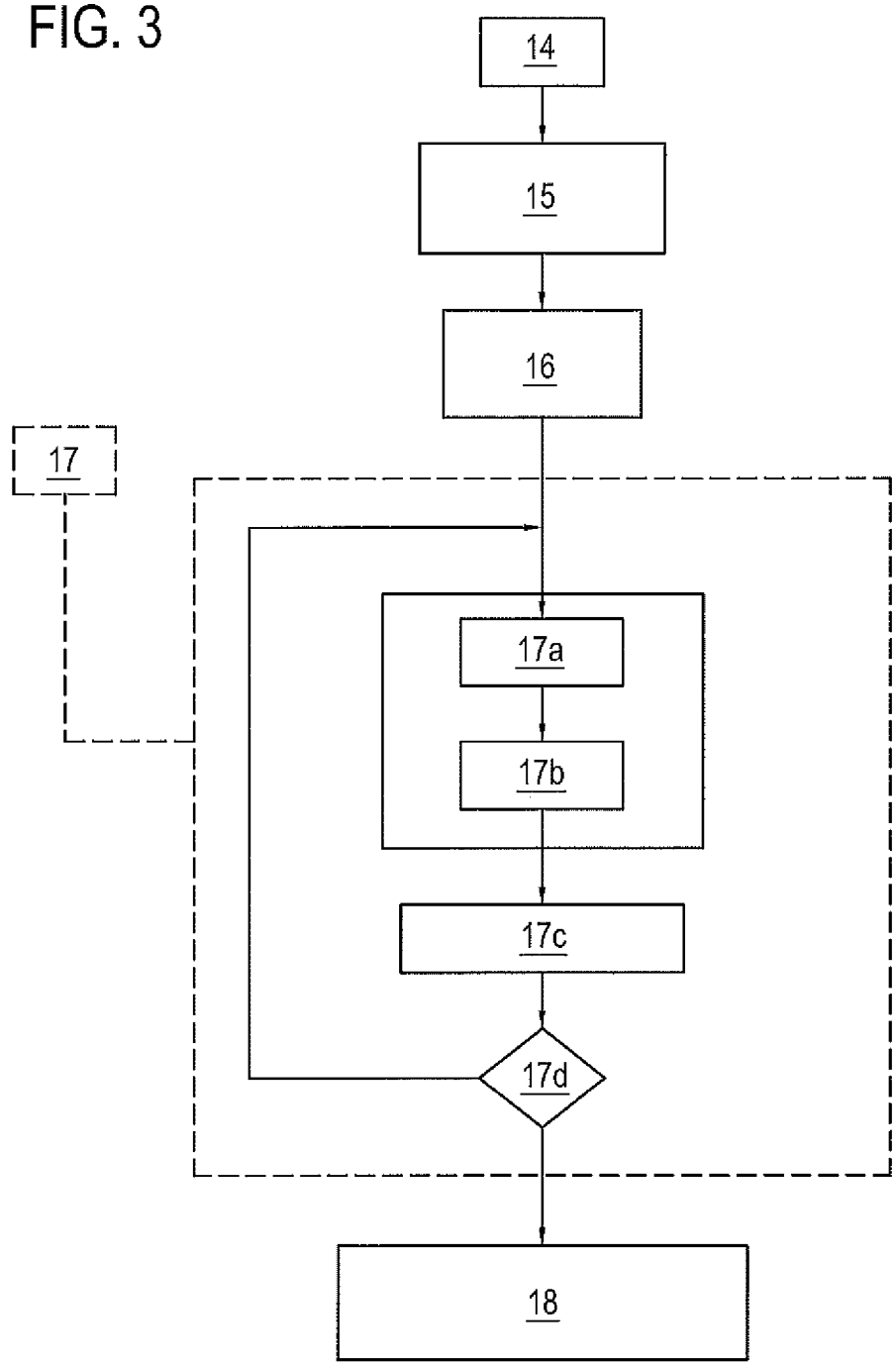
FIG. 3 is a diagram of the steps which characterise a method for measuring odours according to this disclosure.

During training, the method for measuring odours comprises the steps of:

picking a sample of gas characterised by a high concentration of odour (step schematically labelled 14 in FIG. 3);

estimating the concentration of odour using the at least one sensor 3 located inside the measuring chamber 2 (step schematically labelled 15 in FIG. 3);

diluting the sample of gas (step indicated schematically with 16 in FIG. 3) to reduce the concentration of odour;

flushing ozone (step indicated schematically with 17 in FIG. 3) inside the apparatus 1, to allow the at least one sensor 3 to be reset;

introducing diluted gas inside the measuring chamber 2 for training (step indicated schematically with 18 in FIG. 3) the control unit 6 of the apparatus for recognising the characteristic odour of the gas sample.

Preferably, the ozone flushing step 17 inside the apparatus 1 is controlled by a feedback control (indicated schematically with 17d in FIG. 3) which comprises the steps of:

activating the suction device 5 (step indicated schematically with 17a in FIG. 3);

activating the ozone generator 7 (step indicated schematically with 17b in FIG. 3);

measuring the concentration of residual odour (step indicated schematically with 17c in FIG. 3) until reaching a predetermined value indicating the resetting of the at least one sensor 3.

If the concentration of residual odour exceeds the predetermined value, the flushing of ozone 17 continues with the production of ozone by the ozone generator 7 and the generation of a flow of ozone by the suction device 5.

After reaching the predetermined value and resetting the at least one sensor 3, the apparatus 1 is ready for introducing diluted gas, for training 18 the apparatus 1 to recognise the characteristic odour of the gas sample.

The invention claimed is:

1. An apparatus for measuring odours comprising:
    a measuring chamber;
    an intake ducting having an inlet end, in communication with the outside environment, and an outlet end, in connection with the measuring chamber;

a plurality of sensors, positioned inside the measuring chamber and configured for measuring olfactory properties of a gas;

a control unit designed for processing signals coming from the sensors and providing a parameter representing a concentration of the odours measured in the gas, a suction device configured to circulate the gas in the measuring chamber, the suction device generating an intake flow of ambient air flowing through the intake ducting from the inlet end to the outlet end;

a cleaning device, configured for cleaning the intake duct and the measuring chamber of olfactory residue, in order to restore the characteristics of the sensors following a measurement, and configured for generating a flow of ozone inside the intake duct and the measuring chamber, wherein the cleaning device comprises an ozone generator positioned within the apparatus, the ozone generator including a body, a cathode and an anode, the cathode and the anode being housed in the body, wherein the body has an inlet hole and an outlet hole, which are both in fluid communication with the intake ducting, so that the suction device circulates the flow of ozone produced by the ozone generator, wherein the intake ducting includes a first branch, extending from the inlet end of the intake ducting to the inlet hole of the body, and a second branch, extending from the outlet hole of the body to the outlet end of the intake ducting, so that the ozone generator receives ambient air from the outside environment through the inlet hole of the body, wherein the control unit is configured for controlling both the suction device and the ozone generator, as a function of the concentration of the odours measured in the gas, so that a flow including the intake flow of ambient air sucked from the outside environment through the inlet hole and the flow of ozone generated by the ozone generator is provided to flush the sensors until resetting thereof, wherein the ozone generator is arranged in the intake ducting between the inlet end open to the outside environment and the measuring chamber, the suction device being arranged downstream of the measuring chamber, wherein the control unit is programmed for activating the ozone generator and the suction device, upon flushing the sensors, and for deactivating the ozone generator and the suction device, upon sensing the resetting of the sensors.

2. The apparatus according to claim 1, wherein the cleaning device is configured to generate a controlled flow of ozone.

3. The apparatus according to claim 1, wherein the control unit is connected to the ozone generator for varying in a controlled fashion the rate of production of ozone.

4. The apparatus according to claim 1, wherein the cathode is connected to the high voltage generator in direct current.

5. The apparatus according to claim 1, wherein the cathode and the anode are in a point plane configuration.

6. The apparatus according to claim 1, wherein the control unit is connected to a current measuring device for measuring an etrical current delivered by the high voltage generator and is programmed for comparing the measured value of the electrical current with a reference value for the electrical current delivered by the high voltage generator, and is programmed for varying the voltage between the electrodes in responce to said comparison, for varying the ozone production rate.

7. The apparatus according to claim 1, wherein the cleaning device is located at the inlet end of the intake duct.

8. The apparatus according to claim 1, wherein the ozone generator is positioned inside the apparatus and is configured to generate ozon inside the intake duct.

9. The apparatus according to claim 1, wherein the ozone generator includes an electrical current generator which generates an electrical current delivered to the anode and the cathode, wherein the control unit is connected to the current generator to control the electrical current delivered by the electrical current generator.

10. A method for measuring odours comprising the following steps:

introducing a gas, by means of an intake ducting connected to a suction device, inside a measuring chamber, the measuring chamber forming part of an apparatus;

measuring olfactory properties in the gas using a plurality of sensors located inside the measuring chamber;

processing signals coming from the sensors and providing a parameter representing a concentration of the olfactory properties measured in the gas;

cleaning the intake ducting and the measuring chamber of olfactory residue, in order to restore the characteristics of the sensors following a measurement, wherein the cleaning step comprises generating a flushing of ozone in the intake ducting and in the measuring chamber, through an ozone generator including a body and positioned within the apparatus, the ozone generator including a cathode and an anode, the cathode and the anode being housed in the body, wherein the body has an inlet hole and an outlet hole, which are both in fluid communication with the intake ducting, so that the suction device circulates the flow of ozone produced by the ozone generator, wherein the ozone generator receives, at the inlet hole of the body, ambient air from the outside environment, wherein, in the cleaning step, a control unit controls both the suction device and the ozone generator, as a function of the concentration of the olfactory properties measured in the gas, so that the sensors are flushed with a flow including the ambient air sucked from the outside environment through the inlet hole and the flow of ozone generated by the ozone generator, until resetting of the sensors, wherein the control unit activates the ozone generator and the suction device, for flushing the sensors, and deactivates the ozone generator and the suction device upon sensing the resetting of the sensors, wherein the ozone generator is arranged in the intake ducting between the inlet end open to the outside environment and the measuring chamber, the suction device being arranged downstream of the measuring chamber.

11. The method according to claim 10, wherein the flushing of ozone occurs in a controlled manner, to control a quantity of ozone circulating in the measuring chamber.

12. The method according to claim 10, comprising the following steps:

measuring an electrical current delivered by the high voltage generator;

variation of a voltage between cathode and anode as a function of a deviation of the measured electrical current relative to a current reference value, for controlling the ozone production rate.

13. The apparatus according to claim 1 wherein the body has an internal volume, and wherein the cathode includes a first electrically conducting element protruding in the internal volume of the body.

14. The apparatus according to claim 13, wherein the first electrically conducting element of the cathode elongates between a first end, facing the anode, and a second end, opposite the first end, wherein the first end of the first electrically conducting element of the cathode has a tapered shape.

15. The apparatus according to claim 13, wherein the internal volume of the body extends from the inlet hole to the outlet hole alomng a longitudinal direction, and wherein the first electrically conducting element of the cathode is elongate in a transversal direction.

16. The apparatus according to claim 13, wherein the anode includes a second electrically conducting element, the second electrically conducting element including a flat surface.

17. The apparatus according to claim 13, wherein the first electrically conducting element of the cathode faces a second electrically conducting element of the anode inside the internal volume of the body.

18. The apparatus according to claim 1, wherein the inlet hole is aligned with the outlet hole along a longitudinal direction, to define a longitudinal path of the gas from the inlet hole to the outlet hole,wherein the cathode is connected to a first wall of the body, and the anode is connected to a second wall of the body, the first wall opposing the second wall along a transversal direction perpendicular to the longitudinal direction.

19. The apparatus according to claim 1, wherein the control unit is configured for keeping the suction device and the ozone generator activated, until the concentration of the odours measured in the gas reaches a predetermined value.

20. The method according to claim 10, wherein in the cleaning step the control unit keeps the suction device and the ozone generator activated, until the concentration of the odours measured in the gas reaches a predetermined value.

* * * * *